United States Patent
Foser

[19]

[11] Patent Number: 6,139,318
[45] Date of Patent: Oct. 31, 2000

[54] COLOR KEY

[75] Inventor: Hanspeter Foser, Balzers, Liechtenstein

[73] Assignee: Ivoclar AG, Schaan, Liechtenstein

[21] Appl. No.: 09/428,099

[22] Filed: Oct. 27, 1999

Related U.S. Application Data

[60] Provisional application No. 60/113,324, Dec. 22, 1998.

[30] Foreign Application Priority Data

Nov. 5, 1998 [DE] Germany ............................. 198 51 137

[51] Int. Cl.[7] .................................................. A61C 19/10
[52] U.S. Cl. ............................................................. 433/26
[58] Field of Search ........................................ 433/26, 163

[56] References Cited

U.S. PATENT DOCUMENTS

| | | | |
|---|---|---|---|
| 1,518,608 | 12/1924 | Short | 433/26 |
| 2,765,534 | 10/1956 | Bloom et al. | 43/26 |
| 2,805,478 | 9/1957 | Adams | 433/26 |
| 5,261,815 | 11/1993 | Pozzi | 433/26 |
| 5,482,459 | 1/1996 | Yarocesky et al. | 433/26 |
| 5,588,834 | 12/1996 | Resk et al. | 433/26 |
| 5,725,372 | 3/1998 | Leon | 433/26 |
| 5,989,022 | 11/1999 | Yamamoto et al. | 433/26 |

FOREIGN PATENT DOCUMENTS 34 29 927 A1   2/1986   Germany .

*Primary Examiner*—Todd E. Manahan
*Attorney, Agent, or Firm*—John L. Thompson; Alan S. Korman

[57] ABSTRACT

A color key for selecting a proper color for artificial teeth has a base with receiving sockets and insert members having a first end and a second end. The first end is receivable in the sockets. Sample elements are provided whereby each one of the insert elements has one of the sample elements connected to the second end. The sample elements consist of and are produced in the same manner as the dental replacements. The sample elements have a first surface and a second surface, wherein the first surface has a texture matching the texture of a natural tooth and a curvature matching the curvature of a natural tooth. The second surface is flat and smooth.

15 Claims, 3 Drawing Sheets

COLOR KEY

This Appln claims the benefit of U.S. Provisional No. 60/113,324 filed Dec. 22, 1998.

BACKGROUND OF THE INVENTION

The present invention relates to a color key, especially as an aid for selecting the proper color of artificial teeth and as a communication means for restorative dentistry, wherein the color key comprises a plurality of insert members to be inserted into a base and having at their ends a respective sample element.

Such color keys are known from U.S. Pat. No. 5,643,589. Such color keys have been successively used in practice for the purpose of providing flexibility with respect to color selection and patient-specific individualization but also with respect to different focal points of different dental practices and dental labs.

With respect to increased requirements regarding natural appearance of artificial teeth it is desirable to provide color keys which provide improved reproducible results by direct comparison with the present natural teeth and an esthetically improved restoration result.

In this context a plurality of color keys are known. An example of such a color key is known from German Offenlegungsschrift 34 29 927. In this color key, the support elements are removably attached and between the support element and the dental material an opaque layer is arranged so that the color and structure of the support element is not visible through the dental material.

Furthermore, it has been suggested to provide a plurality of bases for the support elements that are then detachably connected to one another. In this solution the two bases can be positioned in various orientations to one another.

Each insertable element can be removed from the known color key so that basically a comparison between the natural and artificial teeth is possible by placing the insert element with the sample tooth adjacent to the natural tooth. In most cases, the insert element, for reasons of available space, and the lip area of the patient must be placed at a slant adjacent to the natural tooth so that due to the different light exposure of the artificial tooth and natural tooth a different visual effect will result. Only a few patients are able to visualize and compensate the differences so that the actual color that was determined by the color key will often deviate from the desired result.

Even though it is known that for proper visual matching the use of indirect natural light is optimal, the optimal illumination situation cannot be realized or realized only with difficulty in different dental practices or dental labs, especially since in most cases artificial light sources are used which provide proper illumination for other work to be performed in the dental practice or dental lab.

Even when using identical spectral photometric curves, same sample elements always appear differently when a textured or structured sample element is compared to a smooth or planar surface.

In the so-called painting technique used in wide areas of tooth restoration, it is common to employ colors which differ greatly from the main dental material. It is also desirable to evaluate such colors which, however, has not been possible in the past with known color keys. This is also true for color nuances used for dental materials for the neck of the tooth and for transparent materials.

It is therefore an object of the present invention to provide a color key of the aforementioned kind which allows for an improved evaluation during selection of an artificial tooth including its nuances and is less sensitive with respect to different illumination situations.

SUMMARY OF THE INVENTION

According to the present invention, the sample elements, consisting of the same material and produced in the same manner as the dental replacements, i.e., artificial teeth and/or the restoration material or medium, and the insert members end in such sample elements having a surface which is textured so as to match the texture of a natural tooth and is especially curved and having another surface, especially the backside, that is planar (flat) and smooth.

Inventively, it is especially favorable that for producing the sample elements exactly the same materials are used as for the actual dental replacement. Identical color additives with identical spectrometric curves are used in both cases and the production process with respect to powder preparation, firing, but also with respect to different batches of the ceramic powder are used in both cases. This provides the necessary requirement that the sample elements have optical identity with the artificial teeth so that no color deviations are to be observed.

It is inventively especially advantageous that one surface of the sample element is textured so as to match the texture of a natural tooth while the other surface is flat or planar and smooth. The textured and curved surface thus provides the possibility to test the impression which the identically produced artificial tooth would have later at the same location. On the other hand, the flat smooth surface at the backside improves the evaluation of only the color since it can be positioned more easily such that reflections are prevented. The planar non-textured surface is especially important for determining the color of the prepared tooth stump and provides an inventive improvement over already known prior art color keys.

When using known color keys, an additional second sample has been used conventionally for the color stump to be prepared. This is disadvantageous with regard to the required expenditure.

Inventively, it is suggested that for the selection of the color of the artificial tooth both aspects can be taken into consideration, i.e., on the one hand, the actual color selection, respectively, the color selection of the prepared tooth stump via the planar, smooth surface, while the appearance of the artificial tooth can be evaluated by turning over the inventive sample element.

In this context it is especially favorable that the sample element or the sample plate is comprised of the identical dental material, whereby, however, the front and backside have different appearances especially in very bright light, so that patients can very precisely evaluate the difference between the color itself and visual appearance of the same color sample when realized in the corresponding tooth restoration.

According to an especially favorable design, it is suggested that the sample elements are pivotably connected to the insert member. For this purpose, the upper part of the insert member is embodied as a sample holder onto which the sample element or the sample plate can be placed while the lower portion is a shaft. Both parts are then connected by a joint that allows pivoting by 90° to both sides.

With this design it is possible to place the sample surface or the sample element in the exact angular position required by the natural tooth in the mouth of the patient (upper jaw or lower jaw) whereby the pivot joint can extend between the incisors and the lip. This allows for an improved evaluation and also further reduces sensitivity with respect to different illumination situations.

According to a further preferred embodiment the base part for the sample teeth is detachably connected to a further base part for tooth enamel samples. This allows to provide, in addition to the sample teeth, to provide special samples for enamel and special effect materials. Such special samples preferably are not tooth-shaped but wedge-shaped. In this context it is also favorable to operate with identical color additives for the sample and the original and to also employ the same manufacturing process.

The detachability of the base part for special effect or enamel materials from the base part for the sample teeth allows separate handling so that, if needed, the dentist can attach the further base part in order to provide, for a patient who is more discerning and requires higher quality work, an additional possibility for color nuances while less discerning patients can be served with the base part comprising only sample teeth and the thus available samples of, for example, 6 or 12 sample teeth colors which are provided at the top side or bottom side of the base part.

However, the inventive device also simplifies storage. For storing, the two base parts are simply inserted into one another, whereby it is preferred that the insert members are designed such that each base part can be handled separately without sharp-edged projections.

A very ergonomic design of the double arrangement of the two-part base results when the individual base parts taper toward their facing sides, i.e., toward the side where the attachment sockets are arranged. Ease of manipulation required for safe insertion of the insert members in their receiving sockets can be further improved by providing grip depressions at each base part at the respective free end whereby the grip depressions provide for ease of attachment and detachment of the two base parts. Furthermore, the double arrangement allows also for individual adaptation to the respective needs of the user. For example, in this manner, it is also possible to combine colors of different manufactures as a color key so that the range for color selection is improved.

The preferred light curvature of the top side and the bottom side of the base part provides an improved manipulation since the curvature is designed to match the curvature of the palm.

Preferably, the insert members for the enamel and dentin material are also designed to be pivotable and are thus provided with a corresponding joint so that they can be placed especially close to the natural teeth in order to facilitate evaluation.

Surprisingly, the inventive color key provides at least partially metameric effects i.e., the property of compensating spectrally different color impressions that induce the same color sensation, by employing the texture and planar surfaces of the same material, to find a color match.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 3.

Figure 1:
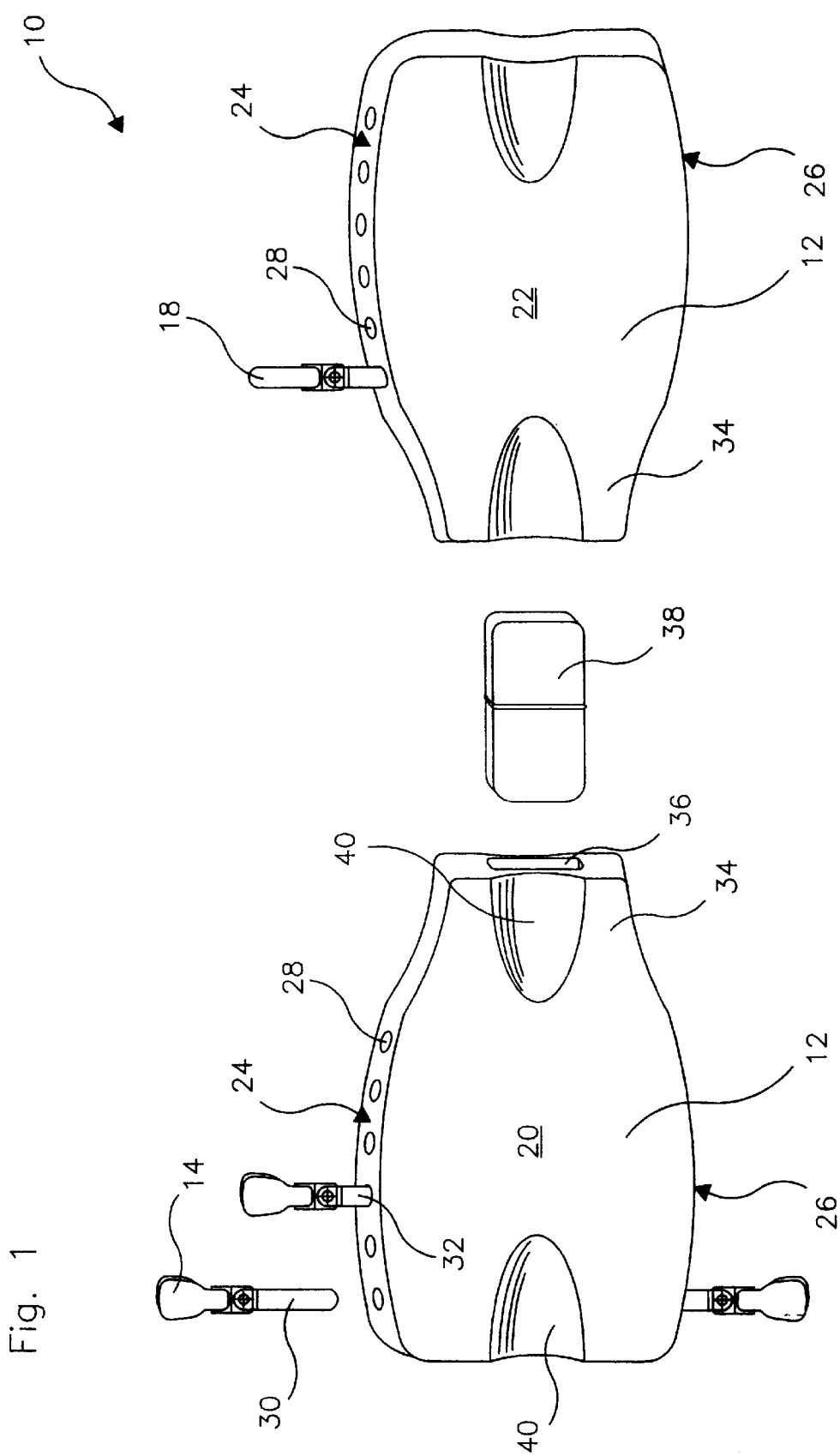
FIG. 1 is a schematic perspective view of the inventive color key.

The color key 10 represented in FIG. 1 has a base with base part 12 for color sample teeth 14 and a base part 16 for enamel samples 18. Both base parts 12 and 16 are substantially mirror-symmetrically embodied and have matching front and back sides whereby FIG. 1 shows only the front sides 20 and 22.

Each base part 12 and 16 has a top side 24 and a bottom side 26. The two sides 24 and 26 are provided with receiving sockets 28 embodied as blind bores. In the represented embodiment 6 receiving sockets 28 for insert members are arranged adjacent to one another at the top side and the bottom side.

The sides 24, 26 are slightly curved in the area of the receiving sockets 28. Since the sockets extend preferably perpendicularly to the top side, the insert members 30, 32 thus diverge so that they can be easily gripped.

According to modified embodiment it is suggested that the insert members 30, 32 extend parallel to one another whereby it is understood that the spacing of the receiving sockets 28 must be accordingly adapted.

The base parts 12 and 16 have adjacent to the area of the sockets 28 a connecting area 34 which tapers. The connecting area 34 has a relatively large socket 36 at its end face which comprises a considerable portion of the end face. A matching socket is provided at the end face of the other base part 16. Accordingly, for the color key 10 comprised of the two attached base parts 12,16 a dumb bell shaped and thus ergonomic design that can be gripped without causing fatigue results.

The sockets 36 match the shape of a connecting member 38 that is inserted with one half respectively completely into the sockets 36 of the base 12 and 16. The connecting member 38 is inserted without play so that a certain amount of force must be overcome to remove the base parts from the connecting member and to separate the two base parts 12 and 16.

The base parts 12 and 16 furthermore have at their front sides 20 and 22 and symmetrically thereto on the non-represented backside grip depressions 40 which facilitate detachment of the parts 12 and 16 but also facilitate the handling of the color key 10 in general. All edges and corners of the base part 12, 16 are rounded in order to provide for easy handling whereby furthermore smooth surfaces are preferred so that the soiling tendency is reduced. Due to the rounded and pleasing design, despite the smooth surfaces, a safe handling is ensured.

The sockets 28 in FIG. 1 are shown round for ease of representation. However, it is preferred to provide a shape that deviates from a circular form and for example, corresponds to the shape of the receiving socket of FIG. 2, i.e., is substantially rectangular.

Figure 2:
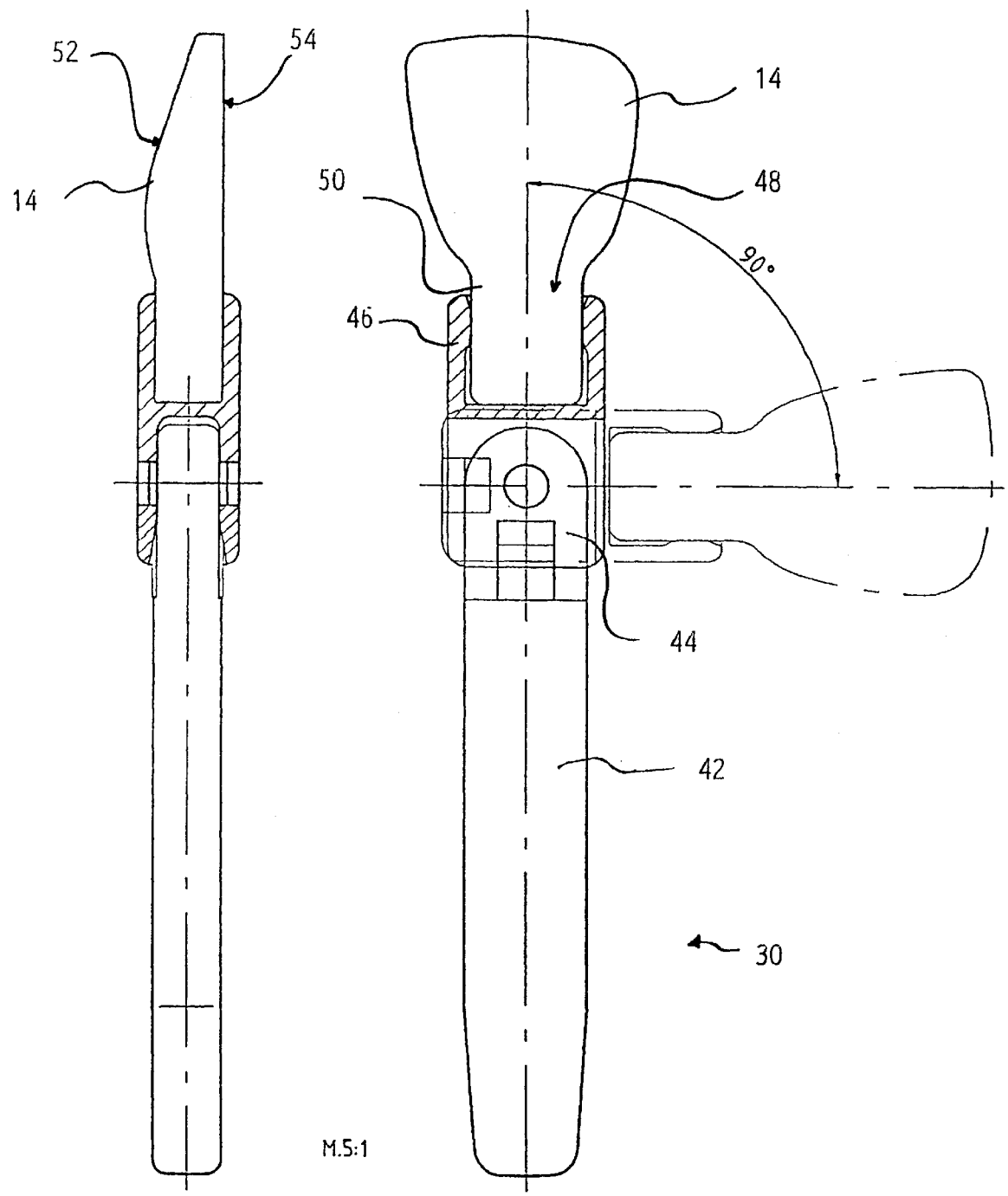
FIG. 2 is a partially sectioned side view and a front view of a first inventive insert member for the color key according to FIG. 1.

In FIG. 2 an insert member 30 is shown in two views, i.e., a front view and a side view. Each insert member has a shaft 42 which is insertable into sockets 28 and is securely held therein when the base part 12 is moved into any desired position.

Each insert member 30 has preferably a joint 44 that connects the shaft 42 to the holder 46. The holder 46 receives the sample tooth 14 whereby in the shown embodiment the sample 14 with its tooth neck is secured without play in a respectively designed receiving element 48 of the holder 46.

The joint 44 is designed such that the holder 46 with its sample tooth 14 can be pivoted in both directions by 90°. When using the sample tooth of insert member 30, the joint 44 can thus be laterally pivoted into a pivot position so that the shaft 44 is a lateral grip portion for the sample tooth 14, whereby, however, the effective height below the sample tooth 14 is reduced, for example, by one third.

Preferably, the holder 46 snaps into the shaft 42 in the straight position of joint 44 in order to prevent that the sample tooth 14 inserted into the base 12 can be moved laterally.

The side view representation according to FIG. 2 illustrates the front side 52 of the sample tooth 14 with its textured surface and especially its contour in order to match as closely as possible a natural tooth. The backside 54 is planar and provided with a smooth surface. By selectively rotating the insert member 30, despite the use of the identical dental material for the sample tooth 14, an evaluation of the different aspects of the selected color can be provided.

Figure 3:
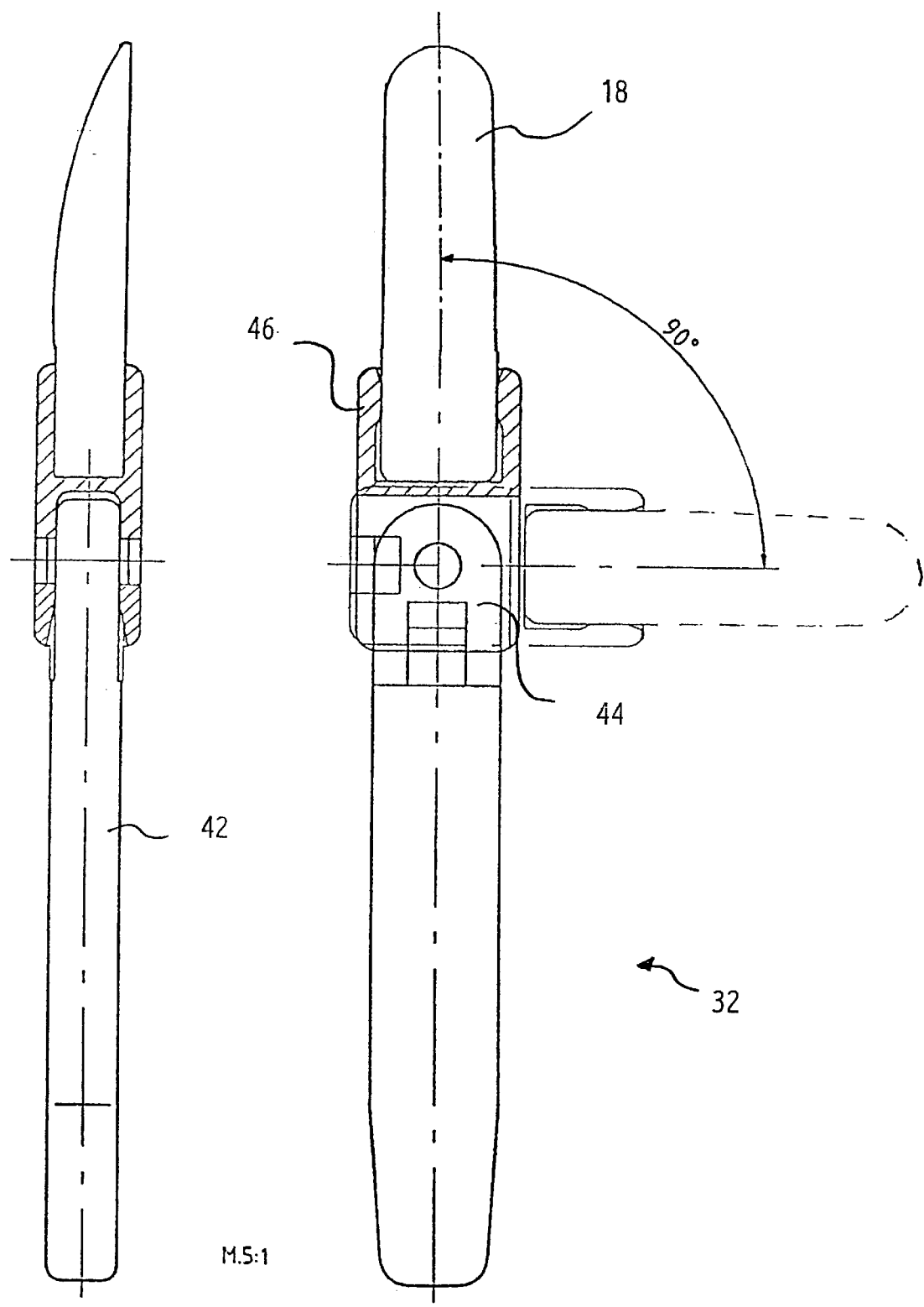
FIG. 3 is a partly sectioned side view and a front view of a first inventive insert member for the color key according to FIG. 1.

FIG. 3 shows a corresponding member 32 but for enamel materials. This insert member 32 is also provided with a pivot joint 44 that allows a pivoting action.

Instead of the sample tooth 14 an enamel sample 18 is inserted into the insert member 32 whereby the holder 46 corresponds to the design according to FIG. 2, i.e., to the design for receiving a sample tooth. The enamel sample 18 is substantially rod-shaped and tapers towards its tip. It can be used as a sample for enamel, effect and special materials but also certain colors of the tooth neck. The sample is deliberately not designed in a tooth shape since such colors are used only for special purposes, and an easily recognizable difference to the sample teeth is thus provided.

What is claimed is:

1. A color key for selecting a proper color of a dental replacement, said color key comprising:

a base having receiving sockets;

insert members having a first end and a second end, wherein said first end is receivable in said sockets; and sample elements having differing colors received in said second end of said insert elements, wherein each of said sample elements consist of and are produced in the same manner as dental replacements with identical color additives as the dental replacements, each of said sample elements having a first surface and a second surface, both surfaces being exposed for visual inspection when received in the second end of the insert elements, wherein said first surface has a texture matching the texture of a natural tooth and a curvature matching a curvature of a natural tooth, and wherein said second surface is flat and smooth which is especially important for determining the color of the prepared tooth stump.

2. A color key according to claim 1, wherein:

said base consists of a first base part and a second base part;

said first and said second base parts are detachably connected to one another;

said dental replacements comprise artificial teeth and enamel sample pieces;

wherein said artificial teeth are received in said first base part and wherein said enamel sample pieces are received in said second base part.

3. A color key according to claim 2, wherein said base further comprises a securing member detachably connecting said first and said second base parts, wherein each one of said base parts has a receiving socket for receiving said securing member.

4. A color key according to claim 2, wherein said base parts have tapered portions and said receiving sockets are located within said tapered portions.

5. A color key according to claim 2, wherein said base parts each have a top side and a bottom side and wherein said receiving sockets are located at said top side and said bottom side.

6. A color key according to claim 5, wherein said top sides and said bottom sides are elongate and curved.

7. A color key according to claim 2, wherein ends of said base parts facing one another have first grip depressions and wherein ends of said base parts facing away from one another have second grip depressions.

8. A color key according to claim 2, wherein said enamel sample pieces are rod-shaped.

9. A color key according to claim 8, wherein said enamel sample pieces are tapered.

10. A color key according to claim 1, wherein each one of said insert members is comprised of a holder, a shaft and a joint, wherein said holder is pivotably connected by said joint to said shaft.

11. A color key according to claim 10, wherein said holder and said shaft have an aligned position in which said holder and said shaft are coaxial to one another and wherein said joint has a pivot range of 90°, respectively, in opposite directions from said aligned position such that said holder and said shaft have perpendicular end positions.

12. A color key according to claim 11, wherein in said aligned position said holder and said shaft are secured by a snap-in action.

13. A color key according to claim 10, wherein said dental replacements are secured in said holders.

14. A color key according to claim 10, wherein said dental replacements are comprised of dental material and wherein said dental replacements are fastened in said holders by at least one securing action selected from the group consisting of positive locking, frictional action, and adhesive action.

15. A color key according to claim 14, wherein said holders consist of plastic material.

* * * * *